United States Patent
Shiba et al.

(10) Patent No.: US 10,568,521 B2
(45) Date of Patent: Feb. 25, 2020

(54) FLUIDIC PRESSURE ACTUATED OPTICAL PROBES FOR IMPROVED FIELD OF VIEW IN TISSUE IMAGING

(71) Applicant: Santa Clara University, Santa Clara, CA (US)

(72) Inventors: Steven Kiyohiko Shiba, Chico, CA (US); Christian Mariano, San Jose, CA (US); Eric Sabelman, Menlo Park, CA (US); Ismail Emre Araci, Santa Clara, CA (US)

(73) Assignee: Santa Clara University, Santa Clara, CA (US)

( * ) Notice: Subject to any disclaimer, the term of this patent is extended or adjusted under 35 U.S.C. 154(b) by 112 days.

(21) Appl. No.: 15/982,796

(22) Filed: May 17, 2018

(65) Prior Publication Data

US 2018/0333054 A1 Nov. 22, 2018

Related U.S. Application Data

(60) Provisional application No. 62/508,796, filed on May 19, 2017.

(51) Int. Cl.
| | |
|---|---|
| *G02B 6/36* | (2006.01) |
| *A61B 5/00* | (2006.01) |
| *G02B 1/06* | (2006.01) |
| *A61B 1/00* | (2006.01) |

(52) U.S. Cl.
CPC .......... *A61B 5/0084* (2013.01); *A61B 1/0019* (2013.01); *A61B 5/0066* (2013.01); *G02B 1/06* (2013.01); *A61B 2562/0233* (2013.01)

(58) Field of Classification Search
USPC ........................................................ 385/118
See application file for complete search history.

(56) References Cited

U.S. PATENT DOCUMENTS

| | | | |
|---|---|---|---|
| 5,577,992 A | 11/1996 | Chiba et al. | |
| 6,081,388 A | 6/2000 | Widl | |
| 2007/0156021 A1 | 7/2007 | Morse et al. | |
| 2014/0221753 A1* | 8/2014 | Tearney | A61B 1/041 600/167 |
| 2016/0114482 A1 | 4/2016 | Lessing et al. | |
| 2018/0168729 A1* | 6/2018 | Pratten | A61B 18/1492 |
| 2018/0249888 A1* | 9/2018 | Kucharski | A61B 1/018 |
| 2018/0252380 A1* | 9/2018 | Kitayama | B62J 6/02 |

\* cited by examiner

*Primary Examiner* — Eric Wong
(74) *Attorney, Agent, or Firm* — Lumen Patent Firm

(57) ABSTRACT

An optical probe having a controlled viewing angle lens tip is provided that includes an elastomer lumen, where the elastomer lumen includes internal dividers disposed to separate the elastomer lumen into a plurality of channels, a lens that is sealably attached to a distal end of the elastomer lumen, where each channel is disposed to operate as an independent hydraulic channel, where an angle of the lens relative to a central axis of the elastomer lumen is positioned according to a state of pressure in each independent hydraulic channel, and a hydraulic generator, where the hydraulic generator is disposed to pressurize each hydraulic channel to a defined state as set by a computer input from a to computer.

10 Claims, 5 Drawing Sheets

GRIN

PDMS membrane

Fiber optic cable

FLUIDIC PRESSURE ACTUATED OPTICAL PROBES FOR IMPROVED FIELD OF VIEW IN TISSUE IMAGING

CROSS-REFERENCE TO RELATED APPLICATIONS

This application claims priority from U.S. Provisional Patent Application 62/508,796 filed May 19, 2017, which is incorporated herein by reference.

FIELD OF THE INVENTION

The present invention relates generally to optical probes. More particularly, the invention relates to pressure actuated lens steering in optical probes for improved field of view, for applications such as endoscopy or optical coherence tomography.

BACKGROUND OF THE INVENTION

The field-of-view (FoV) of traditional forward looking optical probes used in tissue imaging is limited with the area of the imaging lens. The efforts to improve the FoV of the forward-looking imaging probes for in-vivo applications rely on MEMS technologies, which makes them complex and high cost.

What is needed is a durable, miniature, cost effective optical probe that can change the viewing angle to improve the field of view for in-vivo imaging applications

SUMMARY OF THE INVENTION

To address the needs in the art, an optical probe having a controlled viewing angle lens tip is provided that includes an elastomer lumen, where the elastomer lumen includes internal dividers disposed to separate the elastomer lumen into a plurality of channels, a lens that is sealably attached to a distal end of the elastomer lumen, where each channel is disposed to operate as an independent hydraulic channel, where an angle of the lens relative to a central axis of the elastomer lumen is positioned according to a state of pressure in each independent hydraulic channel, and a hydraulic generator, where the hydraulic generator is disposed to pressurize each hydraulic channel to a defined state as set by a computer input from a computer.

In one aspect of the invention, the elastomer lumen further includes a protective material housing along at least a portion of a length of the elastomeric lumen.

According to another aspect of the invention the material of the elastomeric lumen can include PDMS, Polyurethane, TPU, epoxy, Silicone, or silicone-hydrogel.

In a further aspect of the invention, the hydraulic channel has a hydraulic material that can include index match fluid, water, oil, and air.

In a further aspect of the invention, the hydraulic channel has a hydraulic material that can include a pre-polymer of PDMS, Polyurethane, TPU, epoxy, Silicone, or silicone-hydrogel.

In a further aspect of the invention the lens can be a half-ball lens, a gradient index lens, bi-convex, a plano-convex lens, a bi-concave lens, or a plano-concave lens.

In yet another aspect of the invention, the lens includes a material such as polymers, or glass.

According to one aspect of the invention, the lens is configured to receive, to output, or to receive and to output electromagnetic radiation.

In another aspect of the invention further includes a membrane disposed between lens and the distal end of the elastomeric lumen.

According to one aspect the invention further includes a fiber optic cable disposed along the center axis of the elastomeric lumen, where the fiber optic cable is disposed for optical signal emission and collection.

DETAILED DESCRIPTION

Figure 1A:
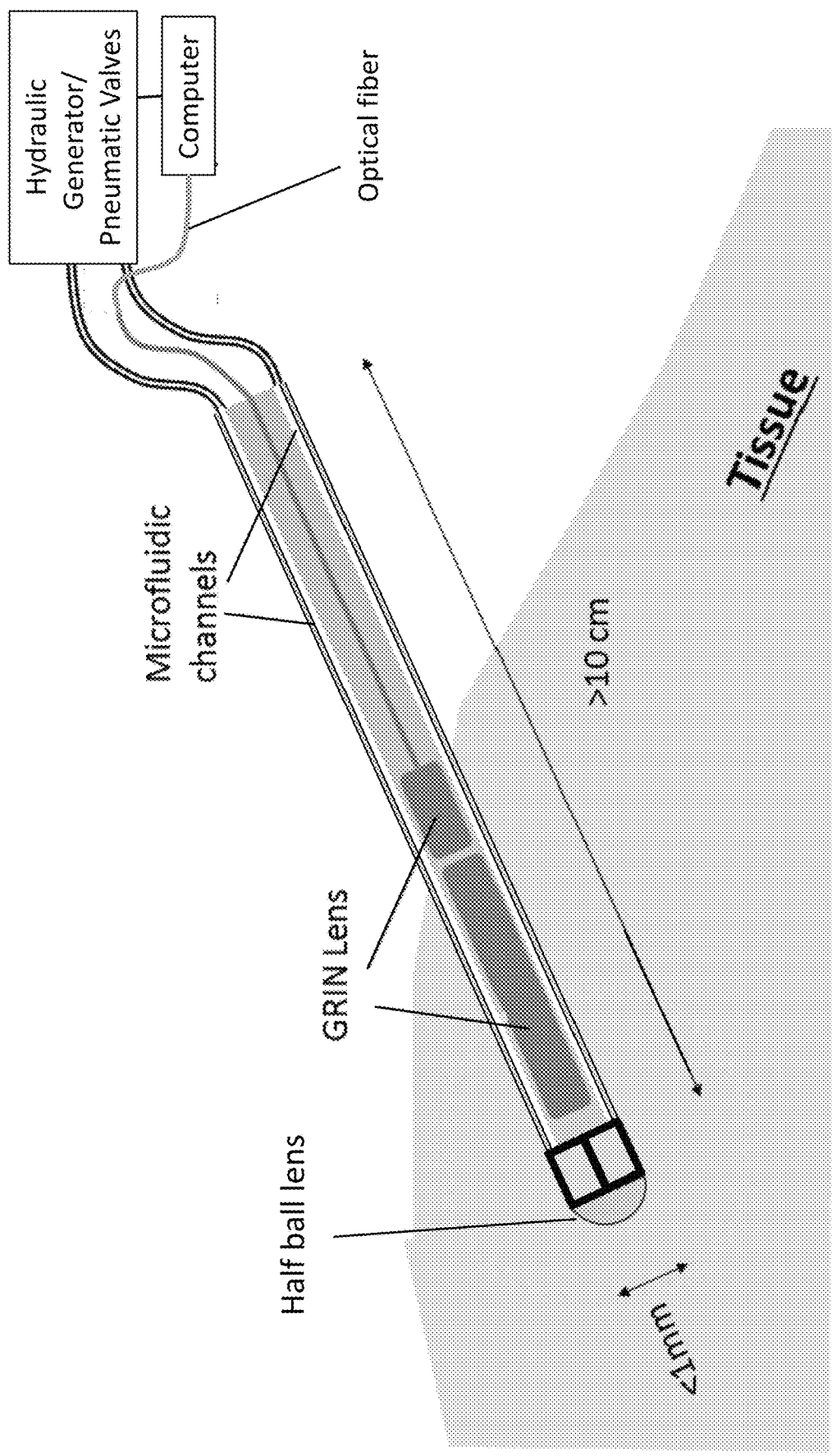
FIGS. 1A-1D show (1A) a schematic drawing of the optical probe, (1B-1C) schematic drawing of an example optical probe having variable a viewing angle, where the fluidic channels are created using a soft elastomeric material, where the soft elastomeric material is shown as PDMS, according to one embodiment of the invention.

The current invention provides a durable, miniature, cost effective optical probe that can change the viewing angle to improve the field of view for in-vivo imaging applications (e.g. OCT, endoscopy etc.). The probe is actuated by fluidic pressure using micromechanical deflection of elastomeric membrane walls under the control of pneumatic valves. The probe can be readily utilized by clinicians during complex surgical, therapeutic, and diagnostic procedures.

According to one embodiment, the invention utilizes a microfluidic pressure driven scanning forward viewing lens probe. A multi-chambered elastomeric base (MEB) is pressurized to achieve scanning motion of the lens. This approach offers significant advantages over existing technologies. The lack of rotary-based mechanics within the current invention increases its durability and allows for a smaller probe to be used. The main strength of the invention is for tissue imaging where the lens rotation is performed on a central axis hence does not cause tissue damage when rotating. In addition, due to the small/flexible nature of pressure driven microfluidic channels and fiber optic cables, where there is no limitation to the length or shape of the probe. Further, the lack of electrical components within the probe increases the safety and reduces the overall risk in using our design. This makes the device immune to electromagnetic interference and enables our probes to be used with instruments such as MRI. Finally, as the invention is not rotating multiple mirrors on different axes, the invention is able to overcome the issue of complex image reconstruction that is required in some of the existing technologies.

Provided herein is an optical probe having a controlled viewing angle lens tip is provided that includes an elastomer lumen, where the elastomer lumen includes internal dividers disposed to separate the elastomer lumen into a plurality of channels, a lens that is sealably attached to a distal end of the elastomer lumen, where each channel is disposed to operate as an independent hydraulic channel, where an angle of the lens relative to a central axis of the elastomer lumen is positioned according to a state of pressure in each independent hydraulic channel, and a hydraulic generator, where the hydraulic generator is disposed to pressurize each hydraulic channel to a defined state as set by a computer input from a computer.

In one aspect of the invention, the elastomer lumen further includes a protective material housing along at least a portion of a length of the elastomeric lumen. As some examples of the hydraulic material in the chambers that can include index match fluid, water, oil, and air. In a further example, the hydraulic fluid in the pneumatic channels is a hydraulic material that can include a pre-polymer of PDMS, Polyurethane, TPU, epoxy, Silicone, or silicone-hydrogel.

According to one aspect of the invention, the lens is configured to receive, to output, or to receive and to output electromagnetic radiation.

Figure 1B:
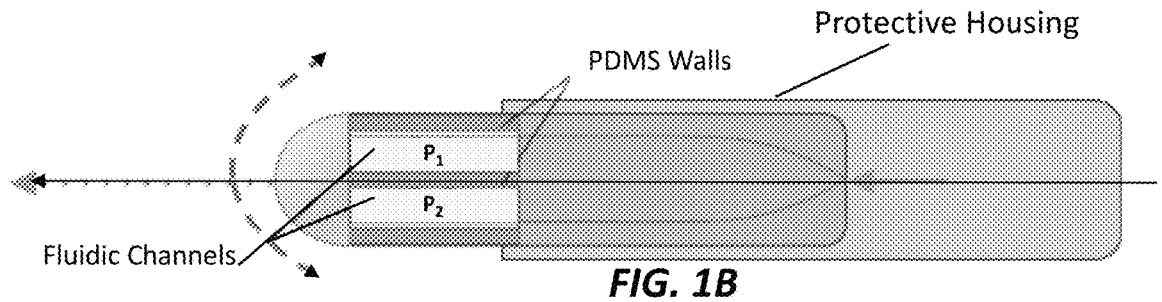
Figure 1C:
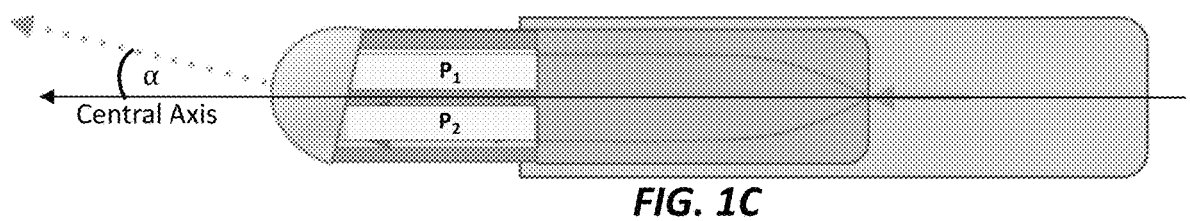
Figure 1D:
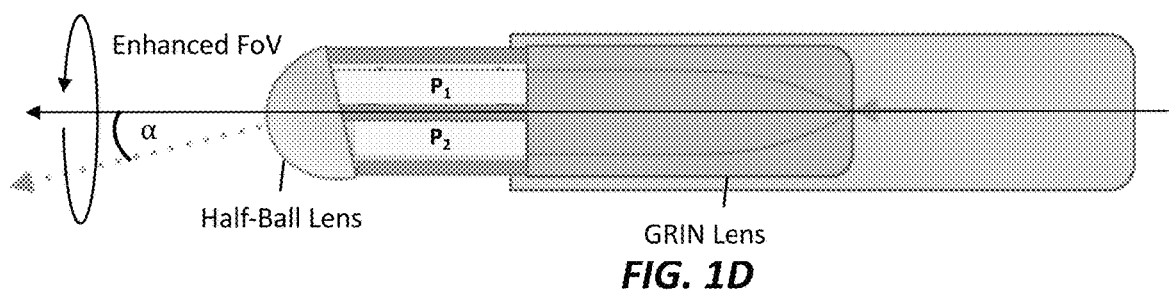
Figure 2:
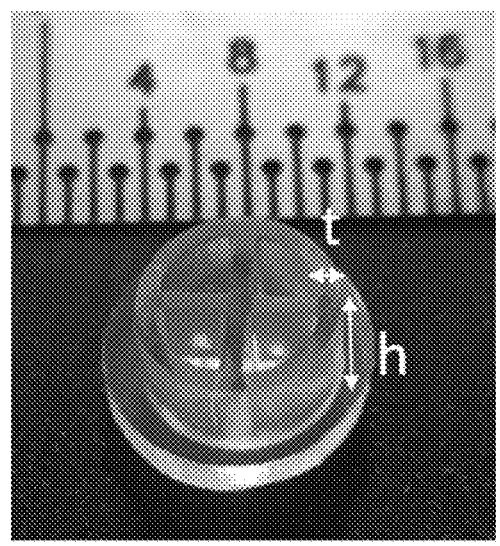
FIG. 2 shows a photograph of the multi-chamber elastomeric base (MEB), where the wall thickness (t) and base height (h) are shown, according to one embodiment of the invention.

Schematic drawings of various embodiments of exemplary probes are shown in FIGS. 1A-1D. In these schematics, the fluidic channels are formed between thin elastomeric walls, which is one key aspect of the invention. One embodiment of an MEB is shown in FIGS. 1B-1D. These examples of the MEB show a cylindrical shaped holder for optical elements such as lenses or mirrors. In these examples, the MEB is shown as separated into four chambers, where pressurizing any one of the chambers will cause an angle change of the optical element on the distal end of the elastomeric lumen.

Figure 3A:
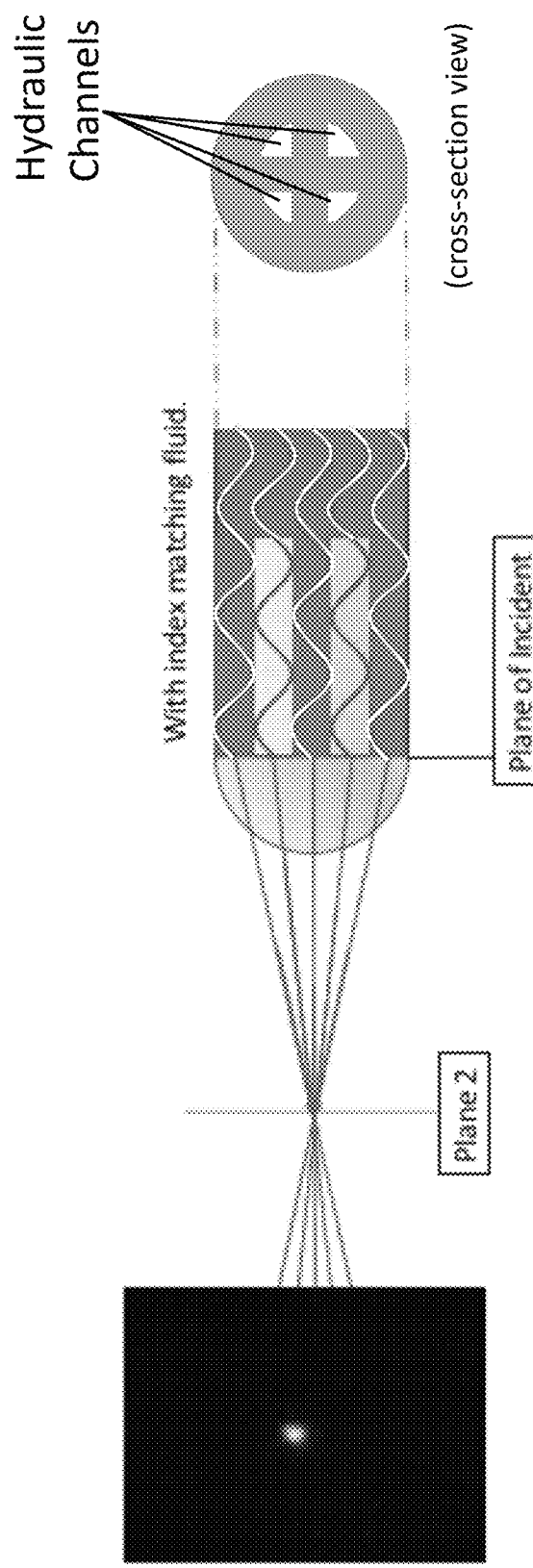
FIGS. 3A-3B show schematic drawings of the effect of index matching fluid in the pneumatic channels, according to the current invention.
Figure 3B:
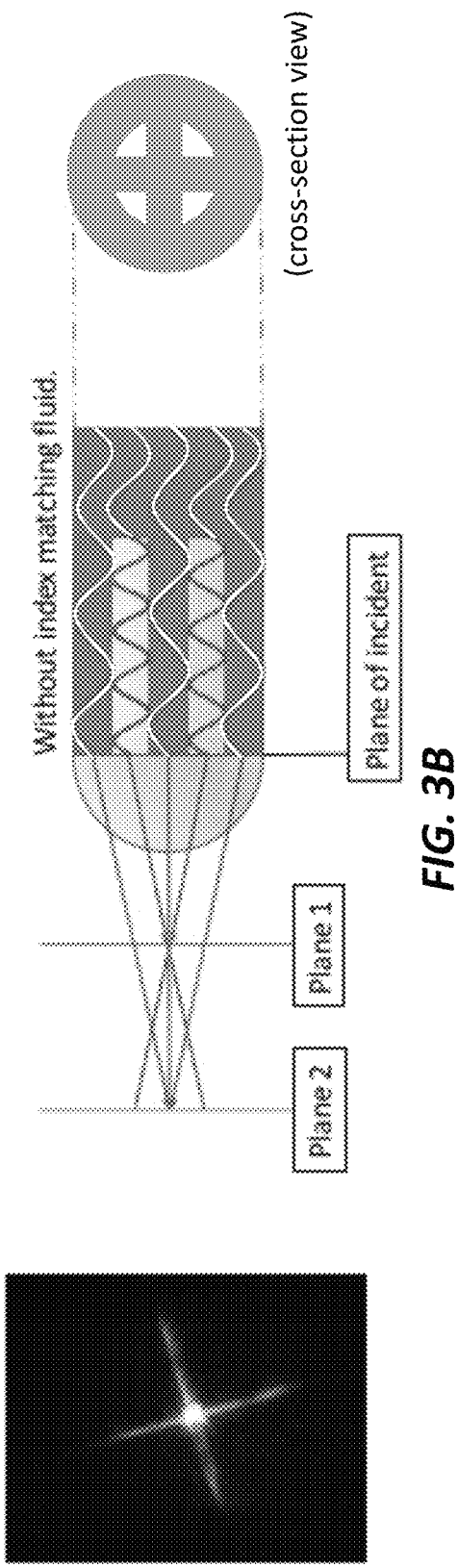

In one aspect of the invention, the image quality is improved by using an index matching liquid inside the chambers of MEB, as shown in FIGS. 3A-3B. According to the current invention, the lens changes the angle of light to create a focus point. The farther away from the center of the lens that light enters, the greater the change in angle the lens makes to the light. Because of the refractive index difference between air and PDMS, two focus points are created: one where the light going through the chambers is focused, and one where the light going through the crosses is focused (see FIG. 3B). When the chambers are filled with index matching liquid this effect is eliminated, as shown in FIG. 3A.

In further aspects of the invention, wide ranges of elastomeric materials can be utilized for fabrication of the MEB, which can include ECO-Flex™, PDMS, Polyurethane, TPU, epoxy, Silicone, and silicone-hydrogel.

Some of the geometrical/physical parameter variations that can be changed and are provided herein. For example, there can be 2, 3, 4, or more fluidic chambers with individual microfluidic connections in an MEB. The thin walls can be 1-500 μm thick. The MEB can be 0.1-10 mm in diameter. The height of the MEB can be 1-100 mm. The young's modulus of the MEB material can be 10 kPa to 10 MPa. Multiple MEB's can be stacked on top of each other to increase total angular range like a C-curve or a S-curve. MEB can have a rigid sleeve to eliminate radial expansion. This will constrain the expansion along probe axis in a linear motion hence improve the efficiency. The material can be transparent.

Figure 4A:
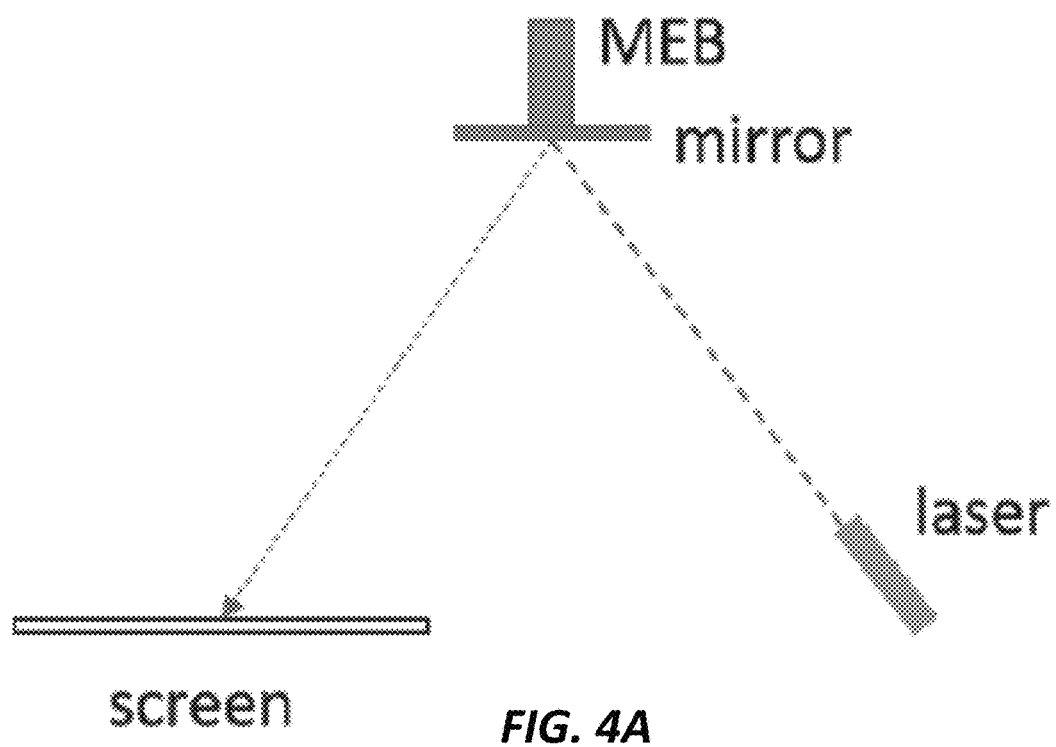
FIGS. 4A-4B show (4A) the setup used to demonstrate the angle change using MEB and a mirror, (4B) the position of the laser beam after reflected from the mirror, which has an angle dependent on the MEB pressure sequence, according to the current invention.
Figure 4B:
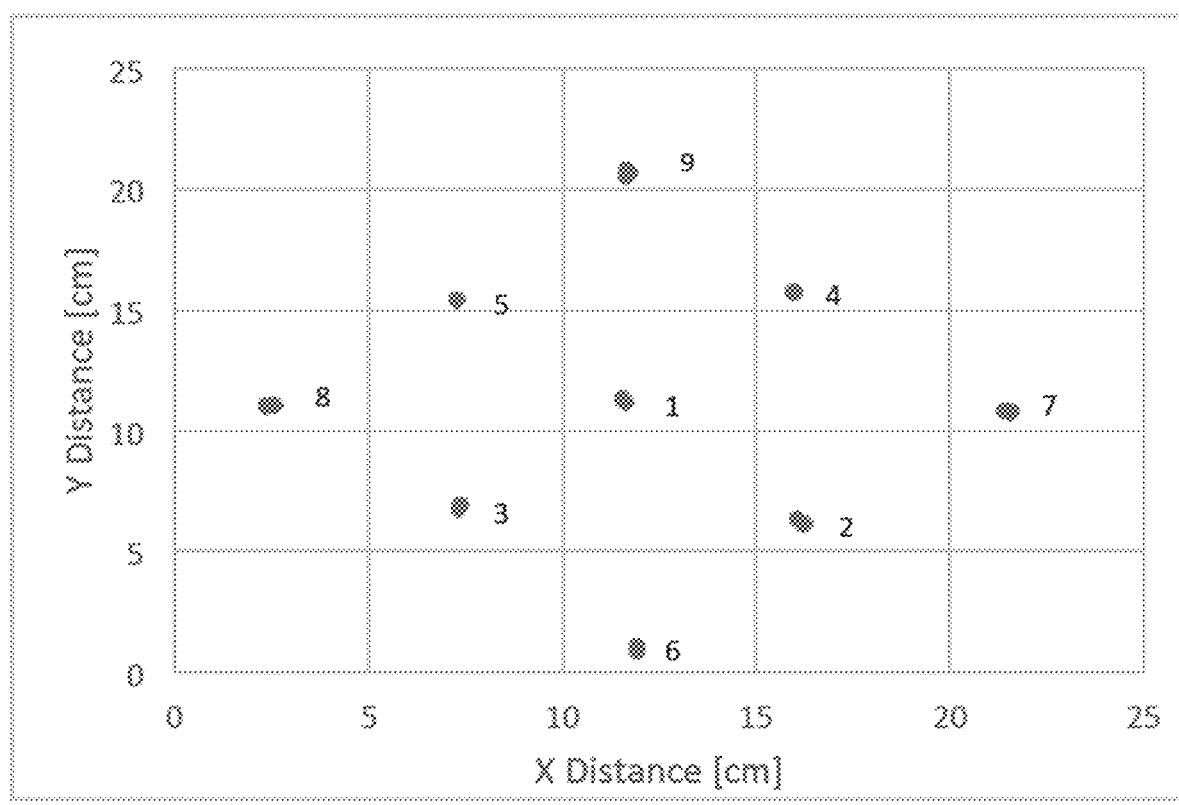
Figure 5A:
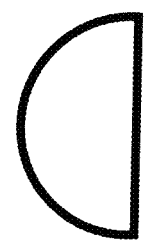
FIGS. 5A-5F show some example lenses that can be included with the MEB, that include a half-ball lens, a gradient index lens, bi-convex, a plano-convex lens, a bi-concave lens, or a plano-concave lens, according to different embodiments of the invention.
Figure 5B:
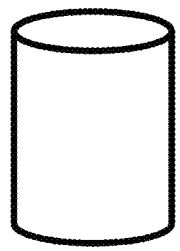
Figure 5C:
Figure 5D:
Figure 5E:
Figure 5F:
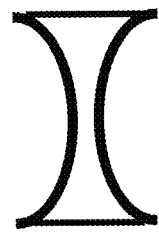

The current invention can be used for mechanical actuation of regular lenses, GRIN lenses and mirrors for a wide range of optical applications where optical beam control is necessary (e.g. optical coherence tomography (OCT), beam steering, adaptive optics, endoscopy, smart phone based imaging). FIG. 4A and FIG. 4B show that when a mirror is used to change the reflection angle of the laser light, the position of the reflected beam can be controlled with high accuracy. FIG. 4A shows the setup used for this experiment, and FIG. 4B shows the position of the beam in x-y coordinates when four different chambers are pressurized sequentially.

FIGS. 5A-5F show some example lenses that can be included with the MEB, that include a half-ball lens, a gradient index lens, bi-convex, a plano-convex lens, a bi-concave lens, or a plano-concave lens, according to different embodiments of the invention. In yet another aspect of the invention, the lens includes a material such as polymers, or glass.

Figure 6A:
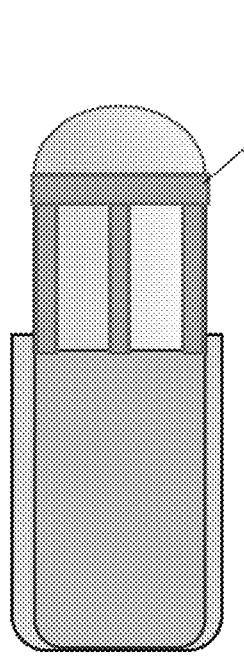
FIGS. 6A-6B show (6A) a membrane included between the lens and the elastomeric lumen, (6B) a fiber optic cable included at the center of the lumen, according to embodiments of the current invention.
Figure 6B:
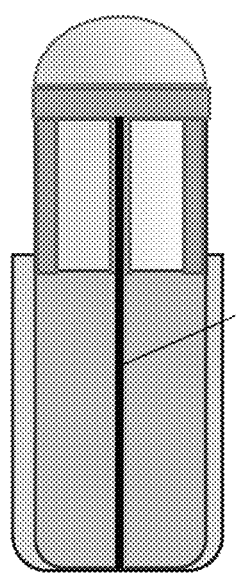

FIGS. 6A-6B a membrane included between the lens and the elastomeric lumen as shown in FIG. 6A. This membrane will help in sealing, bonding and control of the distance between the lens and the other components. FIG. 6B shows a fiber optic cable included at the center of the elastomeric lumen. This fiber optic cable can be used for emission or collection of the optical signal.

The versatility of the invention widens the application possibilities beyond the initial motivation of developing a forward viewing OCT probe for use in neurosurgery. In other embodiments, the probe could be utilized in many other minimally invasive procedures where visualization of a target area and visualization into tissue is required. In one embodiment, a smart-phone based imaging system can be used with the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the invention is useful in applications relating to soft robotics.

All such variations are considered to be within the scope and spirit of the present invention as defined by the following claims and their legal equivalents.

What is claimed:

1. An optical probe having a controlled viewing angle lens tip, comprising:
   a) an elastomer lumen, wherein said elastomer lumen comprises internal dividers disposed to separate said elastomer lumen into a plurality of channels;
   b) a lens that is sealably attached to a distal end of said elastomer lumen, wherein each said channel is disposed to operate as an independent hydraulic channel, wherein an angle of said lens relative to a central axis of said elastomer lumen is positioned according to a state of pressure in each said independent hydraulic channel; and
   c) a hydraulic generator, wherein said hydraulic generator is disposed to pressurize each said hydraulic channel to a defined state as set by a computer input from a computer.

2. The optical probe of claim 1, wherein said elastomer lumen further comprises a protective material housing along at least a portion of a length of said elastomeric lumen.

3. The optical probe of claim 1, wherein a material of said elastomeric lumen is selected from the group consisting of PDMS, Polyurethane, TPU, epoxy, Silicone, and silicone-hydrogel.

4. The optical probe of claim 1, wherein said hydraulic channel comprises a hydraulic material selected from the group consisting of index match fluid, water, oil, and air.

5. The optical probe of claim 1, wherein said hydraulic channel comprises a pre-polymer a hydraulic material selected from the group consisting of PDMS, Polyurethane, TPU, epoxy, Silicone, and silicone-hydrogel.

6. The optical probe of claim 1, wherein said lens is selected from the group consisting of a half-ball lens, a gradient index lens, bi-convex, a plano-convex lens, a bi-concave lens, and a plano-concave lens.

7. The optical probe of claim 1, wherein said lens comprises a material selected from the group consisting of polymers, and glass.

8. The optical probe of claim 1, wherein said lens is configured to receive, to output, or to receive and to output electromagnetic radiation.

9. The optical probe of claim 1 further comprising a membrane disposed between said lens and said distal end of said elastomeric lumen.

10. The optical probe of claim 1 further comprising a fiber optic cable disposed along the center axis of said elastomeric lumen, wherein said fiber optic cable is disposed for optical signal emission and collection.

\* \* \* \* \*